(12) United States Patent
Han et al.

(10) Patent No.: US 7,326,837 B2
(45) Date of Patent: *Feb. 5, 2008

(54) CLINICAL APPLICATIONS OF CRYSTALLINE DIAMOND PARTICLES

(75) Inventors: Chau-Chung Han, Taipei (TW);
Huan-Cheng Chang, Taipei (TW);
Sheng-Chung Lee, Taipei (TW);
Wei-Hao Chen, Taipei County (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 11/361,269

(22) Filed: Feb. 23, 2006

(65) Prior Publication Data

US 2006/0154304 A1    Jul. 13, 2006

Related U.S. Application Data

(63) Continuation-in-part of application No. 11/031,601, filed on Jan. 7, 2005.

(51) Int. Cl.
    *G01N 33/00* (2006.01)
(52) U.S. Cl. .................. 977/705; 977/904; 436/86
(58) Field of Classification Search .............. 435/6, 435/7.1, 287.2, 86; 257/414; 977/705, 904
    See application file for complete search history.

(56) References Cited

U.S. PATENT DOCUMENTS

| 6,607,908 B1 | 8/2003 | Tanga et al. | |
|---|---|---|---|
| 6,677,114 B1 * | 1/2004 | Schneider et al. | ............. 435/4 |
| 2003/0180808 A1 * | 9/2003 | Natsoulis | .................... 435/7.1 |

OTHER PUBLICATIONS

R. Hauert. "A review of modified DLC coatings for biological applications". Diamond and Related Materials 12:583-589, 2003.
L.-C. L. Huang et al. "Adsorption and Immobilization of Cytochrome c on Nanodiamonds". Langmuir 20:5879-5884, 2004.
T. L. Lasseter et al. "Covalently Modified Silicon and Diamond Surfaces: Resistance to Nonspecific Protein Adsorption and Optimization for biosensing". J. Am. Chem. Soc. 126:10220-10221, 2004.
J. B. Miller et al. "Photochemical Modification of Diamond Surfaces". Langmuir 12:5809-5817, 1996.
J. B. Miller. "Amines and thiols on diamond surfaces". Surface Science 439:21-33, 1999.
L. C. Shriver-Lake et al. "Covalent binding of genetically engineered microorganisms to porous glass beads". Analysica Chimica Acta 470:71-78, 2002.
N. Tang et al. "Current Developments in Seldi Affinity Technology". Mass. Spec. Rev. 23:34-44, 2004.
K. Ushizawa et al. "Covalent immobilization of DNA on diamond and its verification by diffuse reflectance infrared spectroscopy". Chemical Physics Letters 351:105-108, 2002.
Yu Liu et al. "Functionalization of Nanoscale Diamond Powder: Fluoro-, Alkyl-, Amino-, and Amino Acid-Nanodiamond Derivatives". Chem. Mater., 16(20):3924-3930, 2004.
Chapman. "Pure but not simple". Nature 434:795-798, Apr. 7, 2005.
Kong et al. "High-Affinity Capture of Proteins by Diamond Nanoparticles for Mass Spectrometric Analysis". Anal. Chem 77:259-265, 2005.
Doucette et al. "Protein Concentration and Enzyme Digestion on Microbeads for MALDI-TOF Peptide Mass Mapping of Proteins from Dilute Solutions". Anal. Chem 72:3355-3362, 2000.
Yang et al. "DNA-modified nanocrystalline diamond thinfilms as stable, biologically active substrates". Nature Materials 1:253-257, Dec. 2002.

* cited by examiner

*Primary Examiner*—Maryam Monshipouri
*Assistant Examiner*—Marsha Tsay
(74) *Attorney, Agent, or Firm*—Occhiuti Rohlicek & Tsao LLP

(57) ABSTRACT

A method for profiling proteins in a biological sample by mixing the sample and a diamond-based composition. The diamond-based composition includes a diamond crystallite having a surface that contains chemically derivatized surface groups and a polymer having a plurality of functional groups non-covalently bound to the surface groups. Proteins in the sample are mixed with and allowed to bind to the diamond-based composition. The bound proteins are then profiled.

25 Claims, No Drawings

CLINICAL APPLICATIONS OF CRYSTALLINE DIAMOND PARTICLES

RELATED APPLICATION

This application is a continuation-in-part and claims priority to U.S. patent application Ser. No. 11/031,601, filed on Jan. 7, 2005, the contents of which are incorporate herein in their entirety.

BACKGROUND

Clinical tests are critical to diagnosis and treatment of various diseases. Many chronic diseases can usually be detected by various diagnostic assays long before pathological symptoms are manifested. Indeed, many intractable diseases, such as various forms of carcinoma, can be cured or controlled if detected at an early stage. To this end, individuals are advised to undergo regular professional physical examinations and to perform routine self-examinations. The diagnostic and prognostic value of self examinations are greatly enhanced if interpreted along with analytical assays of disease markers in biological samples, such as saliva, urine, vaginal secretion, sweat, and feces, collected by a patient at home. It is therefore of the utmost importance that biological samples be collected in a manner that is safe for the patient yet will assure the stability of the samples for analysis.

Many strategies have been developed to extract molecular information present in extremely complicated biological samples, such as blood and cell lysates. Most commonly, these involve very time-consuming pre-separation of the mixture into individual analyzable components, e.g. by 2D-PAGE. However, with the advancement of mass spectrometric (MS) techniques, a moderately complicated mixture can be successfully analyzed without prior isolation of individual components. This type of rapid analysis of complex biological samples is particularly valuable in clinical bioanalysis. Thus there is an ongoing need for methods that allow safe, easy, and reliable collection of biological samples by patients themselves on the one hand, and fast separation of crude samples into MS-analyzable fractions on the other.

SUMMARY

The methods described herein are based, in part, on the finding that diamond is highly biocompatible, stable, and can be derivatized to reversibly and selectively bind proteins in a complex biological sample.

Accordingly, in one aspect the invention is a method for profiling proteins in a biological sample by mixing the sample and a diamond-based composition. The method includes mixing the sample with the diamond-based composition, allowing the proteins to bind to the diamond based composition, and profiling the bound proteins. The diamond-based composition includes a diamond crystallite having a surface that contains chemically derivatized surface groups and a polymer having a plurality of functional groups non-covalently bound to the surface groups, the surface groups being amino, carboxyl, carbonyl, hydroxyl, amide, nitrile, nitro, diazonium, sulfide, sulfoxide, sulfone, sulfhydryl, epoxyl, phosphoryl, oxycarbonyl, sulfate, phosphate, imide, imidoester, pyridinyl, purinyl, pyrimidinyl, or guanidinyl groups, and a portion of the functional groups bind to the chemically derivatized surface groups.

The method can further include acidifying the biological sample to reduce its pH to a range of 1-6 (e.g., pH 2-4). The method can also include removing insoluble impurities in the biological sample by centrifugation or filtration prior to the acidifying step.

The diamond composition-bound proteins can be profiled by a chromatographic, spectroscopic, electrochemical, or mass spectrometric method or a combination of these methods. Alternatively, they can be profiled by gel electrophoresis or gel electrophoresis coupled with mass spectrometry. The bound proteins can also be profiled by immunodetection.

Prior to the profiling step, the bound proteins can be enzymatically digested to yield characteristic peptides. The peptides can be profiled by gel electrophoresis or liquid chromatography, either one of which is followed by mass spectrometry.

The method can include eluting the bound proteins from the diamond based composition prior to the step of profiling, where the profiling step can be gel electrophoresis, gel electrophoresis coupled with liquid chromatography-mass spectrometry, or immunodetection. Alternatively, the eluted proteins can be profiled by gel electrophoresis coupled with liquid chromatography-mass spectrometry. The method can further include a step of enzymatically digesting the eluted proteins to yield peptides characteristic of the eluted proteins. After generation of the peptides, these can be profiled, e.g, by gel electrophoresis coupled with mass spectrometry, or liquid chromatography coupled with mass spectrometry.

In another aspect, the invention is a method for detecting a disease-associated protein biomarker in a biological sample. The method includes mixing the sample with the above-described diamond-based composition, allowing the proteins to bind to the diamond based composition, and analyzing the proteins bound to the diamond-based composition to determine the presence or absence of a disease-associated protein biomarker.

The analysis of the proteins can include performing mass spectrometry. The method can also include performing liquid chromatography or gel electrophoresis of the proteins prior to performing mass spectrometry.

The method can also include, prior to the analysis step, enzymatically digesting the proteins bound to the diamond based composition to yield peptides characteristic of the originally bound proteins. The peptides can be analyzed by mass spectrometry. In addition, the method can include performing liquid chromatography of the peptides prior to the analysis by mass spectrometry.

The details of one or more embodiments of the invention are set forth in the the description below. Other features, objects, and advantages of the invention will be apparent from the description and from the claims.

DETAILED DESCRIPTION

The methods described herein are used to profiling proteins and peptides rapidly in a biological sample such as humoral fluids or cellular extracts. The methods take advantage of the non-specific adsorption characteristics of proteins and peptides in the biological sample to the diamond-based composition. Post adsorption, the high specific gravity and the particulate nature of the diamond-based composition facilitate the removal of excess unwanted liquid in the biological sample and allow removal of contaminants by sequential rinsing. The subsequent protein or peptide profiling can be carried out either on proteins bound to the diamond-based composition or on proteins, in solution, that have been eluted from them.

The method includes the techniques of solid phase extraction and elution on a diamond-based composition (SPEED), chemical and enzymatic processing of proteins or peptides on the diamond-based composition, immunoassay of target proteins adsorbed on the diamond-based composition, and proteome-wide analysis of humoral fluids and cellular extracts with the diamond-based composition. The methods described herein can be used for fast biomarker molecule screening and related proteome-wide analyses in a clinical setting.

Diamond-Based Composition

The diamond-based compositions described herein include (1) a diamond crystallite having chemically derivatized surface groups, and (2) a polymer having functional groups. The diamond crystallite is coated with the polymer through non-covalent interaction between the chemically derivatized surface groups and the functional groups.

The term "diamond crystallite" refers to a diamond powder whose size is 1 nm to 100 μm in diameter (e.g., 5 nm to 20 μm). The size of the diamond crystallites is selected based on the applications and the analysis techniques employed. For example, 100 to 500 nm diamond crystallites are most useful for separating diamond-bound biomolecules by centrifugation. As another example, 1 to 100 μm ones are required for column chromatography. The term "diameter" is defined as the distance between the two longest points on a diamond crystallite. The size of a diamond crystallite can also be described by aspect ratio, which is defined as the ratio of the longest to the shortest linear dimensions. For example, the diamond crystallites in Compositions (1) to (4) preferably have an aspect ratio of 1 to 2. The size of diamond crystallites can be measured either by mechanical sieving (for micrometer-sized powders) or by various electron microscopy, e.g. scanning and transmission electron microscopies (for nanometer-sized powders).

To prepare a diamond crystallite of this invention, the diamond surface is first modified to generate chemically derivatized surface groups. The term "chemically derivatized surface group" refers to amino, carboxyl, carbonyl, hydroxyl, amide, nitrile, nitro, diazonium, sulfide, sulfoxide, sulfone, sulfhydryl, epoxyl, phosphoryl, oxycarbonyl, sulfate, phosphate, imide, imidoester, pyridinyl, purinyl, pyrimidinyl, and guanidinyl groups. They can be introduced to the diamond surface using classical organic synthesis procedures with minor modifications. For example, carboxyl groups can be introduced to the diamond surface by oxidative acid treatment as described in Example (1) below. Other chemically derivatized surface groups can be derived from the starting carboxyl group. For example, amide groups can be generated by reacting the carboxylated diamond crystallites in concentrated $NH_3$ solution at room temperature for one day. Amino groups can be introduced to diamond surface by treating carboxylated diamond crystallites in thionyl chloride at 50° C. for one day, followed by ethylenediamine under reflux for one day. Carbonyl groups are generated by first converting carboxyl groups into acyl chloride or bromide groups, followed by an $S_N2$ or $S_N1$ alkylating reaction. For those chemically derivatized surface groups that are ionizable, ionic bonds can be formed between them and functional groups that have ionizable groups of the opposite charge. The term "ionizable group" refers to the chemical group that is capable of forming ions in solution at a given pH. Examples of ionizable groups include amino, carboxyl, hydroxyl, amide, sulfide, sulfhydryl, imide, pyridinyl, purinyl, pyrimidinyl, and guanidinyl groups.

The term "polymer" covers macromolecules such as polypeptide, polysaccharide, nucleic acid, industrial polymers (e.g., polystyrene, polyesters, polyethyleneglycols, and polyvinyl halides), and their derivatives. These polymers must contain a number of functional groups so that they can interact with the chemically derivatized surface groups. For example, a poly-L-lysine with molecular weight of 3,000 to 30,000 (e.g., 10,000) can be employed to coat a carboxylated diamond crystallite. As another example, a poly-L-arginine can also be used. In these two examples, the key functional groups are both amino groups.

The diamond-based composition includes compositions in which the functional groups that are not bound to the chemically derivatized surface groups are unoccupied.

In other diamond-based compositions a crosslinking agent having two or more reactive groups is attached via covalent bonding between the reactive group and one of the unoccupied functional groups. The term "crosslinking agent" refers to heterofunctional chemical crosslinkers, each having two or more reactive groups. One of the reactive groups binds covalently to the functional group of the polymer, whereas another is unoccupied and thus available for further desired manipulation. Examples of such crosslinking agents include sulfosuccinimidyl 4-(N-maleimidomethyl)-cyclohexane-1-carboxylate (SSMCC), γ-maleimidobutyric acid N-hydroxysuccinimide ester (GMBS), N-[α-maleimidocaproyloxy]succinimide ester), N-[α-maleimidocaproyloxy]-sulfosuccinimide ester, ethylene glycolbis(succinimidylsuccinate), and 3-[(2-aminoethyl)dithio] propionic acid, and N-(α-maleimidoacetoxy)succinimide ester. The chemical properties of these crosslinking agents have been well characterized. For example, SSMCC is a heterobifunctional crosslinker. One end of SSMCC reacts with the amino group of a polymer-coated surface, whereas the other end reacts specifically with a sulfhydryl group of a cysteine-containing protein. As another example, GMBS functions as a crosslinking agent between sulfhydryl groups of a polymer-coated surface and lysine amino groups of a protein.

Methods for Protein and Peptide Profiling

The methods described herein for analyzing a biological sample involve mixing the sample and the diamond-based composition to allow proteins in the sample to bind non-covalently to it, followed by profiling i.e., determining the identity of the bound proteins. The term "biological sample" refers to any specimen originated from a living organism. Examples include extracts of cellular contents, tissue biopsy sections, breast milk, gastric fluid, bronchial fluid, cerebrospinal fluid, ascitic fluid, utero-vaginal discharge, urine, feces, semen, menstrual blood, saliva, sputum, and serum. The identity of the proteins bound to the diamond-based composition can be determined by standard analytical methods involving chromatographic, spectroscopic, electrochemical, and mass spectrometric techniques including, but not limited to, MALDI-TOF-MS, capillary electrophoresis, liquid chromatography, sodium dodecyl sulfate-polyacrylamide gel electrophoresis (SDS-PAGE), enzyme linked immuno-sorbent assay (ELISA) and combinations of these techniques.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Diamond crystallites, 5 to 100 nm in diameter, were functionalized by acid treatment following the procedures described in Ushizawa et al. (2002) *Chem. Phy. Lett.* 351: 105-108. Specifically, the diamond crystallites were first heated in a 9:1 (v/v) mixture of concentrated $H_2SO_4$ and $HNO_3$ at 75° C. for 3 days, subsequently in 0.1 M NaOH aqueous solution at 90° C. for 2 hours, and finally in 0.1 M HCl aqueous solution at 90° C. for 2 hours. The resulting carboxylated diamond crystallites were extensively rinsed with de-ionized water and separated by centrifugation with a Kubota 3700 centrifuge at 12,000 rpm. Two stock suspensions, containing 1 mg/mL and 0.1 mg/mL of diamond crystallites, respectively, were prepared with de-ionized water. Carboxylated diamond crystallites (0.07 g) were mixed with poly-L-lysine in boric acid (0.03 g) in a volume of 10 mL. The pH of the mixture was adjusted to pH 8.5 by addition of NaOH aqueous solution to 8.5) and the mixture was incubated for 30 minutes to obtain diamond crystallites coated with poly-L-lysine which contains amino groups. The poly-L-lysine-coated diamond crystallites thus obtained were then thoroughly washed with de-ionized water.

EXAMPLE 2

Poly-L-lysine-coated diamond crystallites (0.07 g) prepared from Example 1 were mixed with SSMCC (2.2 mg), a heterobifunctional crosslinking agent, in 10 mL of phosphate buffer saline at pH 8.5 for one hour, to obtain poly-L-lysine/SSMCC-coated diamond crystallites. After separation of excess SSMCC by centrifugation, the sedimentary diamond crystallites were thoroughly washed with de-ionized water.

EXAMPLE 3

The carboxylated diamond crystallites prepared from Example 1 were used for analyzing human blood serum. Blood serum samples were obtained from healthy males, clotted, and subsequently separated by centrifugation. The serum thus isolated was divided into 50-μl portions and immediately stored in a −20° C. refrigerator until use. Three independent mass analyses of blood serum were conducted to compare:

(1) Conventional method. 1 μL of blood serum was mixed with 50 μL of 4-hydroxy-α-cyanocinnamic acid (4HCCA) matrix solution, and 2 μL of the serum-matrix mixture was deposited on a stainless steel MALDI-TOF-MS probe and air-dried.

(2) ZipTip method. A ZipTip (C18 pipette tip, Millipore) containing resin for binding molecules was first activated following the standard protocol of the manufacturer. 50 μL of blood serum was then passed through the ZipTip repeatedly by pipetting the sample solution (10 μL each) in and out 5 times. After rinsing three times with an aqueous solution containing 0.1% trifluoroacetic acid (TFA) and 5% methanol, the molecules attached to the resin were eluted with a 0.001:1:1 (v/v/v) TFA-acetonitrile-water mixture (10 μL). Half of the eluate was mixed with 2 μL of 4HCCA matrix solution and the mixture was then deposited on the MALDI-TOF-MS probe.

(3) Diamond crystallite method. 10 μL of blood serum was diluted 100-fold with de-ionized water and then mixed with 10 μL of the diamond crystallite suspension (1 mg/mL). After equilibration for 2 minutes, the combined solution was centrifuged for 5 minutes and the supernatant was removed. The precipitate was washed once with de-ionized water (1 mL), collected by centrifugation (3 minutes), and finally mixed with 5 μL of 4HCCA matrix solution. An aliquot (1 μL) of the mixture was deposited on a MALDI-TOF-MS probe for mass spectroscopic measurements.

In the conventional method, each sample was diluted 50-fold directly with 4HCCA matrix solution in order to obtain a mass spectrum with adequate signal-to-noise ratios. The spectrum showed three strong signals at m/z 66440, 33220, and 22150 corresponding to human serum albumin; however, it displayed only two distinct features at m/z 2000-10000. In the serum samples purified with the ZipTip method, many new features emerged in the lower m/z region owing to desalting and pre-concentration of the sample. In the serum samples pretreated with diamond crystallites, similar high-quality mass spectra were obtained even though 10-fold less serum was used for data acquisition. The mass spectrum obtained using the diamond crystallite method had approximately 5-fold higher peak intensity than that of the ZipTip method, and was noticeably richer in spectral features over the entire mass range. Furthermore, the albumin peaks were suppressed to a greater extent with the diamond crystallite method than the ZipTip method. Thus, without compromising the high sensitivity as well as the high selectivity, the entire analysis of each sample was finished in as few as 10 minutes.

These results were unexpected, given the significant improvement in sensitivity and accuracy compared to other existing methods.

EXAMPLE 4

The poly-L-lysine/SSMCC-coated diamond crystallites prepared from Example 2 were used to covalently bind a protein. The crystallites (0.07 g in 10 mL) and 26 μM phosphate-buffered yeast cytochrome c (YCC; 1.6 mg protein in 5 mL of phosphate-buffered saline at pH 6.5) were mixed for one hour. The resulting protein-diamond mixture underwent several cycles of washing with de-ionized water until the supernatant fraction of the sample appeared clear and transparent after centrifugation, showing negligible absorption at 409 nm.

YCC absorbs strongly at 409 nm (the Soret band) and contains a single free sulfhydryl group (cysteine 102) for covalent bonding with SSMCC, a heterobifunctional crosslinking agent. One end of the crosslinking agent reacted with amino groups of poly-L-lysine coated on diamond crystallites, whereas the other end reacted with a sulfhydryl group of a cysteine-containing protein. In the Fourier transform infrared (FTIR) spectrum of YCC immobilized on the 100 nm poly-L-lysine/SSMCC-coated diamond crystallites, both poly-L-lysine and YCC contributed to the observation of the amide I and II bands in the spectrum. The contribution of the latter, however, was deduced semi-quantitatively by proper normalization of the spectrum with respect to the surface C=O absorption bands at ~1800 $cm^{-1}$, followed by subtracting the spectrum of poly-L-lysine in the amide vibration region. Similar analysis applied to YCC on 5 nm poly-L-lysine/SSMCC-coated diamond crystallites indicated that the adsorption density of the covalently immobilized proteins nearly doubled with the aid of SSMCC, compared to the proteins immobilized non-covalently without SSMCC.

A protein stability experiment was also conducted. Two samples, poly-L-lysine/YCC-coated diamond crystallites and poly-L-lysine/SSMCC/YCC-coated diamond crystallites, were deposited separately on Ge(111) wafers and air-dried to generate thin films. The stability of YCC on the thin films was tested using FTIR. The YCC protein on the thin films was so stable that the spectra remained essentially unchanged after 10 cycles of washing. After storage of the sample suspensions at 4° C. for 5 months, the YCC film showed only slight decreases in intensity of both the amide bands, revealing desorption of some non-covalently bound proteins. More remarkably, the poly-L-lysine/SSMCC/YCC film produced a spectrum essentially identical to that of a freshly prepared one, indicating unexpectedly high stability of the immobilized biomolecules.

EXAMPLE 5

Conventional protein concentration by TCA precipitation can be simplified with solid phase extraction and elution on a diamond-based composition (SPEED). With SPEED it is possible to concentrate all proteins in the mixture by adjusting the solution to desired pH, adding diamond-based composition, thorough mixing, incubating for five minutes at room temperature and finally harvesting the proteins adsorbed on diamond crystallites by filtration or centrifugation. The effectiveness of the SPEED method was evaluated by incubating increasing amounts of a diamond-based composition with a constant amount of protein. A total of 5, 10, 20, and 40 µg of the diamond-based composition were added to a solution containing 6 protein standards (0.2 µg each): phosphorylase b, bovine serum albumin, ovalbumin, carbonic anhydrase, soybean trypsin inhibitor, and lysozyme. After incubation for 5 minutes at room temperature, the amount of bound protein was determined by SDS-PAGE. As expected, the amount of bound protein increased along with the amount of added diamond composition. Adsorption of the protein to the diamond composition was essentially complete for the highest amount of diamond composition tested (i.e., 40 µg).

EXAMPLE 6

The effectiveness of the diamond composition in supporting enzymatic digestion and subsequent analysis of the resulting peptides was tested. Bovine cytochrome c was first adsorbed on surface-carboxylated diamond and the protein-laden diamond particles were directly digested with trypsin. A control digestion was performed separately in free solution with the same quantity of bovine cytochrome c and trypsin, but in the absence of diamond particles). Subsequently the resulting peptides were analyzed by mass spectrometry. The resulting mass spectrum obtained from the on-diamond digest was qualitatively and quantitatively similar to that observed for the in-solution digest.

EXAMPLE 7

Freshly collected male urine samples were centrifuged to remove cellular debris and insoluble components. Twenty micrograms of diamond particles (a nominal size of 100 nm in this example) were added to 1.5 ml aliquots of the urine sample. In one 1.5 ml aliquot urine sample, the sample was first acidified with formic acid to a final concentration of 1%, and 20 µg diamond particles was then added to the vial. In another sample, 20 µg of diamond particles were added to the sample, but the pH of the sample was not modified. Both vials were then centrifuged, and the resulting pellet was rinsed to remove inorganic salts. The proteins adsorbed on the diamond particles under these two conditions were then analyzed by SDS-PAGE. The results confirmed the high protein adsorptivity of diamond crystallites, and demonstrated that this adsorptivity is further increased at reduced pH. The method was fast. A total of 40 minutes to obtain the results, including 30 minutes required for SDS-PAGE. Duplicate runs of the same urine sample yielded identical patterns on the gel, indicating the high reproducibility of this procedure.

EXAMPLE 8

A proteome-wide analysis of urine samples is described below. Procedures for handling the urine samples (supernatant) included the steps of:
1) adjusting the pH value of 1 ml urine samples by adding 50 µl of buffer (1M sodium citrate, pH 3 and 5; 1M Tris-HCl, pH 7 and 9; 1M CAPS, pH 11);
2) adding 20 µg of nanodiamonds to each vial;
3) Microcentrifuging and discarding the resulting supernatant;
4) drying the diamond-protein pellets;
5) adding 50 µl ammonium bicarbonate containing 100 ng trypsin to the pellets;
6) incubating overnight at 37° C.;
7) drying the supernatant containing peptide fragments and resuspending the pellet with 10 µl of 0.1% formic acid; and
8) subjecting the peptide mixture to LC/MS/MS analysis for protein identification.

The peptide mass fingerprinting analyses identified more than 50 proteins of human origin, and part of this finding is listed in the following table. Increasing the sample pool to include 20 individuals increased the number of identified proteins to over 120.

TABLE 1

Partial list of urinary proteins identified by LC/MS of 1 ml urine samples concentrated with 100 nm diamond crystallites after adsorption at different pH values. Varying pH values resulted in adsorption of different sets of proteins identified as indicated by the X.

| Protein name | PI | MW (Da) | 3 | 5 | 7 | 9 | 11 |
|---|---|---|---|---|---|---|---|
| protein C inhibitor, chain A | 9.07 | 39681 | X | X | X | X | X |
| epidermal growth factor | 5.62 | 127875 | X | X | X | X | X |
| serum albumin | 5.92 | 69321 | X | X | | | |
| Kininogen | 6.29 | 47871 | X | X | X | X | X |

TABLE 1-continued

Partial list of urinary proteins identified by LC/MS of 1 ml urine samples concentrated with 100 nm diamond crystallites after adsorption at different pH values. Varying pH values resulted in adsorption of different sets of proteins identified as indicated by the X.

| Protein name | PI | MW (Da) | 3 | 5 | 7 | 9 | 11 |
|---|---|---|---|---|---|---|---|
| transferrin | 6 | 53725 | X | | | | |
| GP36b glycoprotein | 6.46 | 40203 | X | | | | |
| Vasorin | 7.16 | 71668 | X | X | X | X | X |
| homocysteine S-methyltransferase | 6.41 | 44942 | X | | | | |
| complement cytolysis inhibitor SP-40 (clusterin) | 5.89 | 52461 | X | X | X | X | X |
| Collagen, type VI, alpha 1 | 5.26 | 108462 | X | X | X | X | X |
| hemoglobin chain alpha | 8.72 | 15248 | | X | | | |
| hemoglobin chain beta | 6.7 | 15930 | X | X | X | X | |
| alpha-1-antitrypsin | 5.56 | 41886 | X | | | | |
| Gelsolin | 5.21 | 52340 | X | | | | X |
| alpha-1-B-glycoprotein | 5.65 | 51908 | X | | | | |
| Prostatic acid phosptatase | 5.89 | 44511 | X | | X | X | X |
| uromodulin (Tamm-Horsfall glycoprotein) | 4.97 | 69692 | X | X | X | | |
| prostacyclin-stimulating factor | 8.25 | 29111 | X | X | X | X | X |
| MBL-associated serine protease(MASP)-2 | 5.39 | 75654 | X | | | | |
| complement S-protein (vitronectin) | 5.55 | 54328 | X | X | X | X | X |
| Immunoglobulin light chain | 5.46 | 23504 | X | X | X | X | X |
| glyceraldehyde-3-phosphate dehydrogenase | 8.57 | 36030 | X | X | X | X | X |
| Cystatin-C protein | 7.86 | 12532 | X | | | | |
| Plasminogen activator, urokinase | 8.92 | 44552 | X | | | | |
| Immunoglobulin heavy chain | 6.75 | 51095 | X | | | | |
| tetranectin | 5.52 | 22552 | | X | X | X | X |
| Bile salt-stimulated lipase | 5.13 | 79617 | | | X | X | X |
| complement C1 inhibitor | 6.09 | 55119 | | | | X | |
| monocyte surface glycoprotein CD14 | 5.84 | 40111 | | | X | X | X |
| actin gamma 1 | 5.31 | 41766 | | | | X | |
| fructose-bisphosphate aldolase | 8 | 39448 | | | | X | X |
| superoxide dismutase | 6.14 | 25865 | | | | X | |
| Mac-2-binding glycoprotein | 5.13 | 65289 | | | | X | |
| osteopontin | 4.37 | 35401 | | | | X | X |
| phosphoglycerate kinase | 8.3 | 44586 | | | | | X |
| II-acetylglucosamine-6-sulfatase | 8.6 | 62042 | | | | | X |
| Alpha enolase | 6.99 | 47008 | | | | | X |
| angiopoietin-related protein-2 | 7.23 | 57068 | | | | | X |

EXAMPLE 9

Immunodetection of proteins. In this operation, diamond crystallites were either uncoated (as control), or coated with mouse antigen or rabbit antigen, respectively, and each experiment was performed in duplicate runs. The diamond pellets were then blocked with skimmed milk, and then one set of three diamond pellets was probed with anti-mouse antibody, and the other set with anti-rabbit antibody. Only two of the six combinations yielded positive chemiluminescence signal, as was expected (i.e., anti-mouse to mouse antigen and anti-rabbit to rabbit antigen). These results demonstrated the high specificity of immunodetection of proteins adsorbed on diamond crystallites.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for profiling proteins in a biological sample comprising:
   mixing the sample and a diamond-based composition, wherein the diamond-based composition includes a diamond crystallite having a surface that contains chemically derivatized surface groups and a polymer having a plurality of functional groups non-covalently bound to the surface groups, the surface groups being carboxyl groups, and a portion of the functional groups bind to the chemically derivatized surface groups;
   binding proteins in the sample to the diamond-based composition; and
   profiling the proteins bound to the diamond-based composition.

2. The method of claim 1, further comprising, prior to the mixing step, acidifying the biological sample to reduce its pH to a range of 1-6.

3. The method of claim 2, wherein the range is 2-4.

4. The method of claim 2, further comprising, prior to the acidifying step, removing insoluble impurities in the biological sample by centrifugation or filtration.

5. The method of claim 1, wherein the proteins are profiled by a chromatographic, spectroscopic, electrochemical, or mass spectrometric method or combinations thereof.

6. The method of claim 1, wherein the proteins are profiled by gel electrophoresis.

7. The method of claim 1, wherein the proteins are profiled by gel electrophoresis coupled with mass spectrometry.

8. The method of claim 1, further comprising, prior to the profiling step, enzymatically digesting the proteins bound to the diamond-based composition to yield peptides characteristic of the originally bound proteins.

9. The method of claim 8, wherein the peptides are profiled by gel electrophoresis coupled with mass spectrometry.

10. The method of claim 8, wherein the peptides are profiled by liquid chromatography coupled with mass spectrometry.

11. The method of claim 1, wherein the proteins are profiled by immunodetection.

12. The method of claim 1, further comprising, prior to the profiling step, eluting the proteins from the diamond composition.

13. The method of claim 12, wherein the proteins are profiled by gel electrophoresis.

14. The method of claim 12, wherein the proteins are profiled by gel electrophoresis coupled with liquid chromatography-mass spectrometry.

15. The method of claim 12, wherein the proteins are profiled by immunodetection.

16. The method of claim 12, further comprising, after the eluting step, enzymatically digesting the proteins to yield peptides characteristic of the eluted proteins.

17. The method of claim 16, wherein the peptides are profiled by gel electrophoresis coupled with mass spectrometry.

18. The method of claim 16, wherein the peptides are profiled by liquid chromatography coupled with mass spectrometry.

19. A method for detecting a disease-associated protein biomarker in a biological sample comprising:
   mixing the sample and a diamond-based composition, wherein the diamond-based composition includes a diamond crystallite having a surface that contains chemically derivatized surface groups and a polymer having a plurality of functional groups non-covalently bound to the surface groups, the surface groups being carboxyl groups, and a portion of the functional groups bind to the chemically derivatized surface groups;
   binding proteins in the sample to the diamond-based composition; and
   analyzing the proteins bound to the diamond-based composition to determine the presence or absence of a disease-associated protein biomarker.

20. The method of claim 19, wherein the analyzing includes performing mass spectrometry of the proteins.

21. The method of claim 20, wherein the analyzing further comprises performing liquid chromatography of the proteins prior to performing the mass spectrometry.

22. The method of claim 20, wherein the analyzing further comprises performing gel electrophoresis of the proteins prior to performing the mass spectrometry.

23. The method of claim 19, further comprising, prior to the analyzing, enzymatically digesting the proteins bound to the diamond-based composition to yield peptides characteristic of the originally bound proteins.

24. The method of claim 23, wherein the analyzing comprises performing mass spectrometry of the peptides.

25. The method of claim 24, further comprising performing liquid chromatography of the peptides prior to performing the mass spectrometry.

* * * * *